US007123725B2

(12) United States Patent
Boesch, Jr. et al.

(10) Patent No.: US 7,123,725 B2
(45) Date of Patent: Oct. 17, 2006

(54) HIGH INTENSITY INFRASONIC TUNABLE RESONANT ACOUSTIC TEST CELL

(75) Inventors: Harold E. Boesch, Jr., Beltsville, MD (US); Bruce T. Benwell, Sumerduck, VA (US); Christian G. Reiff, Arlington, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1046 days.

(21) Appl. No.: 09/749,861

(22) Filed: Dec. 29, 2000

(65) Prior Publication Data

US 2002/0085723 A1      Jul. 4, 2002

(51) Int. Cl.
 *H04R 29/00* (2006.01)
(52) U.S. Cl. .................... 381/58; 381/345; 181/155
(58) Field of Classification Search ............ 381/58–59, 381/345, 66, 64, 337–338, 353–354, 395, 381/162, 71.1, 71, 56, 349, 351, 71.5; 181/181–182, 181/198–199, 155, 166
See application file for complete search history.

(56) References Cited

U.S. PATENT DOCUMENTS

| | | | | |
|---|---|---|---|---|
| 3,550,720 A | * | 12/1970 | Harold | 181/31 |
| 3,990,069 A | * | 11/1976 | Schuman | 340/544 |
| 4,574,632 A | * | 3/1986 | Woolley et al. | 73/571 |
| 4,593,784 A | * | 6/1986 | Flanders | 181/144 |
| 5,131,052 A | * | 7/1992 | Hill et al. | 381/336 |
| 5,475,764 A | * | 12/1995 | Polk | 381/351 |
| 5,734,728 A | * | 3/1998 | Meissner | 381/89 |
| 6,389,146 B1 | * | 5/2002 | Croft, III | 381/345 |
| 6,504,938 B1 | * | 1/2003 | Anderson et al. | 381/335 |

* cited by examiner

*Primary Examiner*—Vivian Chin
*Assistant Examiner*—Lun-See Lao
(74) *Attorney, Agent, or Firm*—Paul S. Clohan, Jr.; Edward L. Stolarun

(57) ABSTRACT

An apparatus and method are provided for high intensity acoustic test cells that employ the Helmholtz resonator principle, incorporating at least one moderately-sized volume or test cell that is tunable to a given infrasonic to low-sonic frequency and generates sound of high intensity with very pure sinusoidal waveforms in this test cell or volume, by varying the geometry of a port which is connected to the test volume and open to either atmosphere or a second or input volume and by introducing to the test volume or the input volume a driving acoustic signal at the given tuned frequency. The apparatus and method are used for testing or performing experiments on materials, structures, devices, products, biological entities or humans at high acoustic intensities and frequencies in the low-sonic to infrasonic ranges.

10 Claims, 3 Drawing Sheets

HIGH INTENSITY INFRASONIC TUNABLE RESONANT ACOUSTIC TEST CELL

BACKGROUND OF THE INVENTION

1. Field of the Invention

The present invention relates to the field of acoustic test chambers or cells. More particularly, the invention is directed to an apparatus and method for providing an acoustic test chamber or cell that achieves, in air, very high-intensity infrasonic to low-sonic frequencies in moderately large test volumes with very pure sinusoidal waveforms.

2. Description of Related Art

High-intensity acoustic test chambers are well known in the art. Previous high-intensity acoustic test chambers capable of operation at fundamental frequencies below 100 Hz include high-intensity flow-modulator-driven non-resonant chambers, standing-wave resonant chambers driven by flow modulators or loudspeakers, and piston-driven sealed chambers.

Each of these known high-intensity acoustic test chambers has significant limitations. High-intensity flow-modulator-driven non-resonant chambers as devices are not capable of efficient operation or the production of reasonably undistorted sound (sine waves) below about 30 Hz.

Standing-wave resonant chambers driven by flow modulators or loudspeakers, by their nature, have strongly non-uniform acoustic fields in their test volumes and require that the test chamber have a long dimension of at least one-half the wavelength of the lowest usable frequency. That is, their long dimension must be at least 11 m's at 30 Hz.

Piston-driven sealed chambers require a mechanical drive to accelerate and decelerate a piston which serves as one wall of a test chamber or test cell. This acceleration/deceleration takes place at very high rates which restricts these devices to very low frequencies and small test volumes, typically less than 1 $m^3$.

SUMMARY OF THE INVENTION

The present invention generates continuous high-intensity acoustic fields with clean sinusoidal waveforms, in air, in a moderately large volume, and in the infrasonic to low-sonic frequency range (1 Hz to 30 Hz).

Embodiments of the present invention employ a test volume as part of a Helmholtz resonator that may include one or more volumes.

For both single-volume and multi-volume embodiments, generation of an infrasonic to low-sonic (e.g., 1 Hz to 30 Hz), very high-intensity, spectrally pure acoustic field in volumes of useful size (e.g., 5 $m^3$) is accomplished by using the volumes themselves as parts of a Helmholtz resonator. These volumes are each directly driven at a chosen frequency and intensity by an external acoustic energy source.

In one embodiment of either a single or multiple volume test cell, each volume is directly driven at a chosen frequency and intensity by a modulated air or gas flow introduced into one of the volumes. In another embodiment of a single or multiple volume test cell, each volume is directly coupled to acoustic transducers. In either embodiment the acoustic field in a given test volume can be tuned to a predetermined driving frequency by varying the geometry of an associated duct/tuning port connected to said volume but otherwise not directly connected to the acoustic energy source. The intensity and spectral purity of the acoustic signal in each volume are enhanced by the resonance of its associated duct/tuning port.

In another embodiment of a multi-volume test cell, each test volume is isolated from an acoustic energy source by means of dividing each Helmholtz resonator volume into two volumes (input volume and test volume) in which the input and test volumes are connected to one another by a duct/tuning port. Air is exhausted from the input volume to the exterior through a long duct or other high acoustic mass. Isolation of the test volume eliminates any possibly undesirable contaminants or characteristics of the air or gas flow (e.g., noxious gases, excessively low or high temperatures) associated with that flow. Further, isolation eliminates the unidirectional gas flow from the acoustic energy source through the resonator duct/tuning port and consequent acoustic losses in the duct associated with turbulence and loss of acoustic mass.

DETAILED DESCRIPTION OF THE PREFERRED EMBODIMENTS

Figure 1:
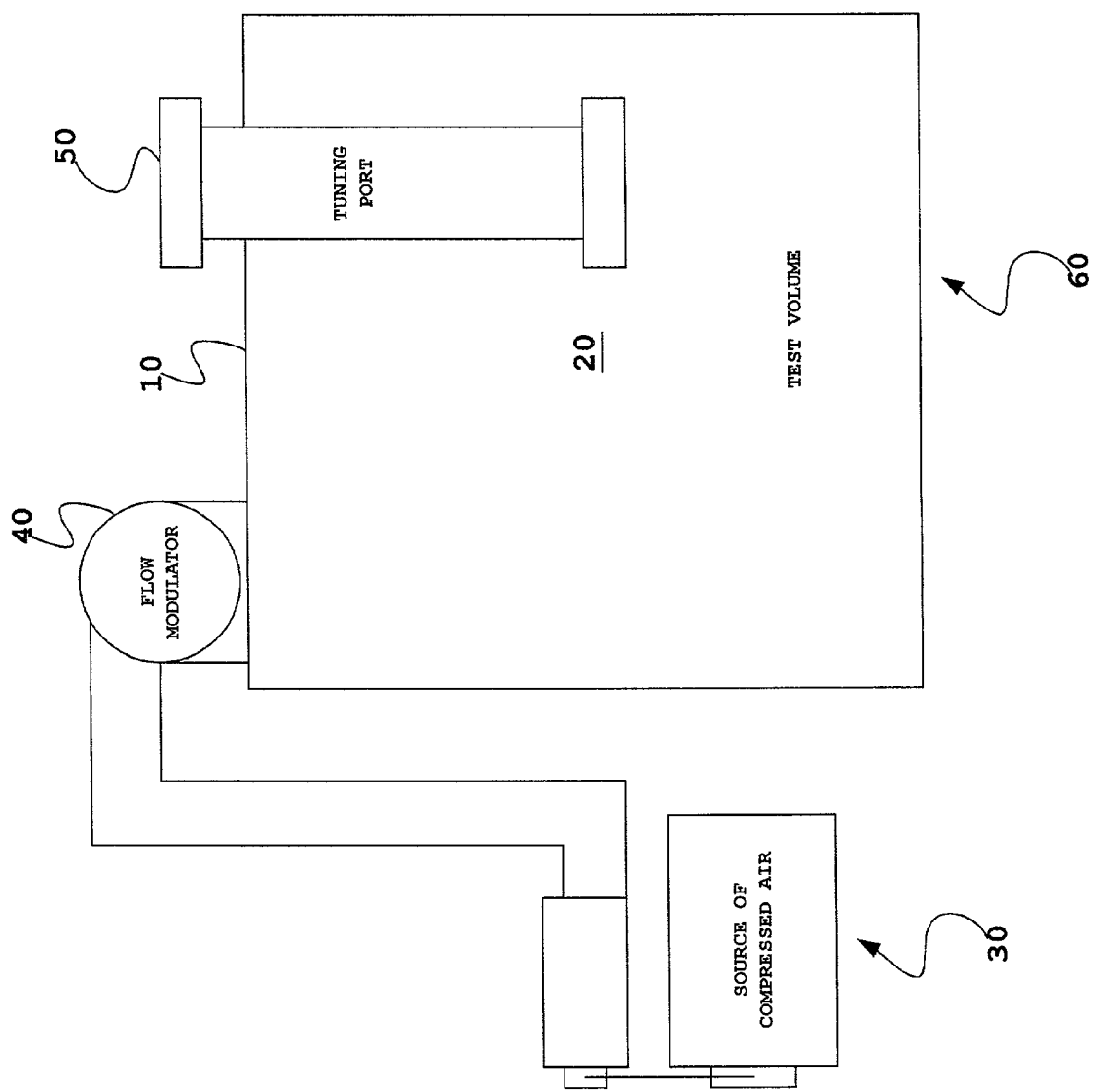
FIG. 1 illustrates an embodiment of the present invention employing a single volume acoustic test cell according to the present invention.

A first embodiment of the present invention, illustrated in FIG. 1, comprises a rigid airtight chamber 10 enclosing a test volume 20, typically about 5 $m^3$. A high-intensity repetitive acoustic signal or air pressure variation, typically with a low fundamental or repetition frequency (single Hz to tens of Hz) is introduced into the test volume 20 of this chamber by means of an acoustic energy source. One such means is a source of compressed air (air compressor) 30 and a flow modulator 40 which periodically varies the flow of compressed air from the source into the volume 20. It is to be understood that the periodic air pressure variation generated by the acoustic energy source means is not restricted to be sinusoidal. The test volume 20 and an associated tuning port or duct 50 that communicates with outside free air constitute a Helmholtz resonator 60 that can be tuned by means of varying the internal length and/or cross section of the tuning port 50 to the frequency that corresponds to the fundamental frequency of the periodically varying air or gas flow from the flow modulator 40 or other acoustic source. The intensity and spectral purity of the sound in the test volume 20 are thereby amplified by the Helmholtz resonance of the volume 20 tuning port 50 combination. The maximum dimensions of the test volume 20 are chosen to be less than one-half of the wavelength corresponding to the maximum operating acoustic frequency of the apparatus. With this choice of maximum dimensions, standing waves are not generated in the test volume 20 and the acoustic field in the test volume 20 is highly uniform.

Figure 2:
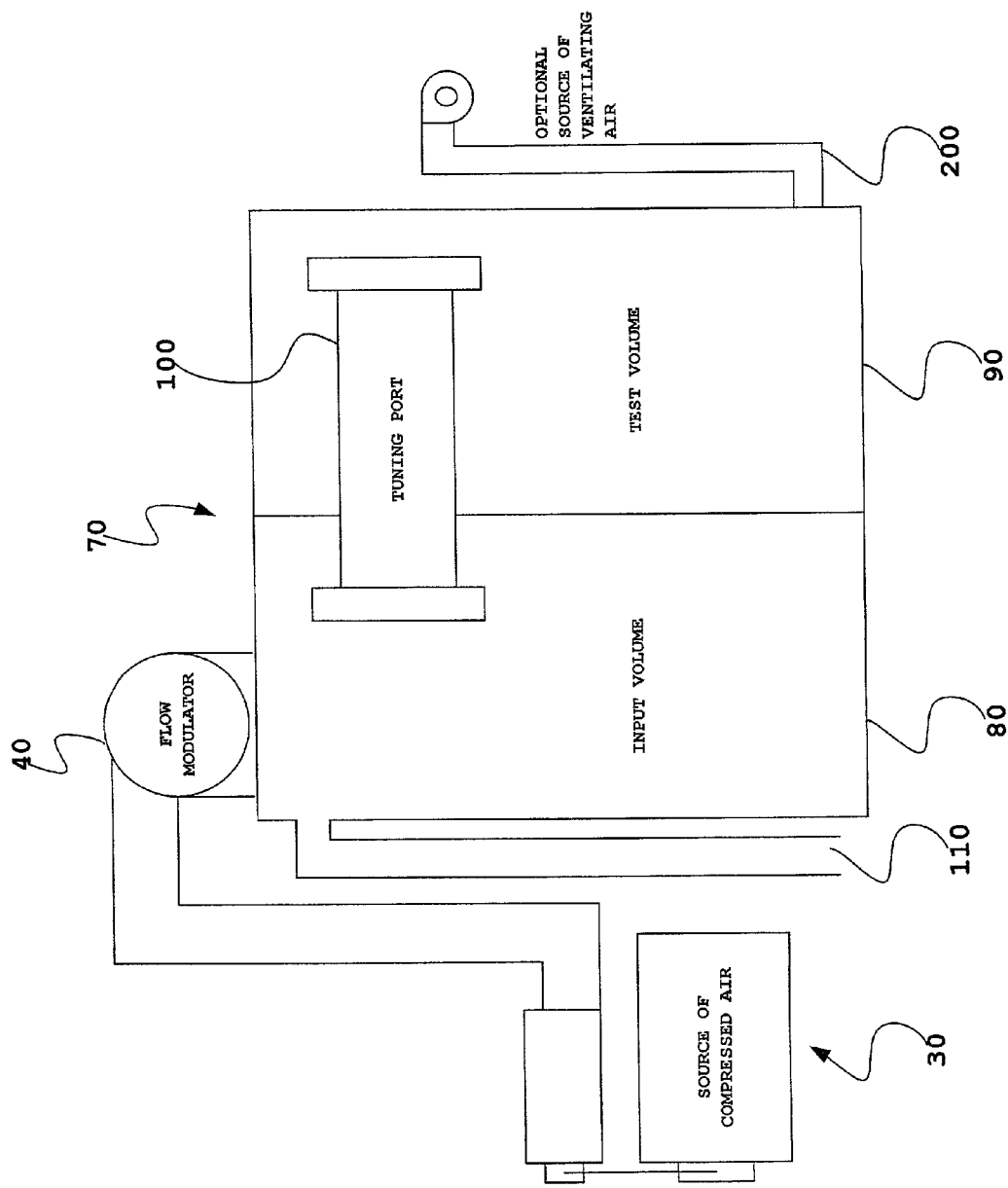
FIG. 2 illustrates another embodiment of the present invention employing a dual-volume Helmholtz resonator test cell driven by a compressed-gas source through a flow modulator or other acoustic source.

Another embodiment of the present invention is illustrated in FIG. 2 and operates in a similar manner. The apparatus illustrated in FIG. 2 includes a rigid chamber 70 enclosing two volumes 80 and 90 connected by a duct/ tuning port 100 which rigid chamber and tuning port as a unit act as a Helmholtz resonator that is tuned by varying the length and/or cross-section of the duct/tuning port 100. In this embodiment the second (test) volume 90, communicates with the first (input) volume 80, only by means of the duct/tuning port 100 and (with the possible exception of an optional relatively low-volume positive-pressure ventilating air input with very high acoustic mass and/or resistance 200) is airtight to air and sound flow to the outside. The unidirectional, or DC, component of the air flow from the flow modulator 40 or other acoustic source and air compressor 30 is exhausted to the outside free air through a long pipe of small diameter 110 that, by virtue of its high acoustic mass, passes only acoustic energy at frequencies below the operating frequencies of the system.

Figure 3:
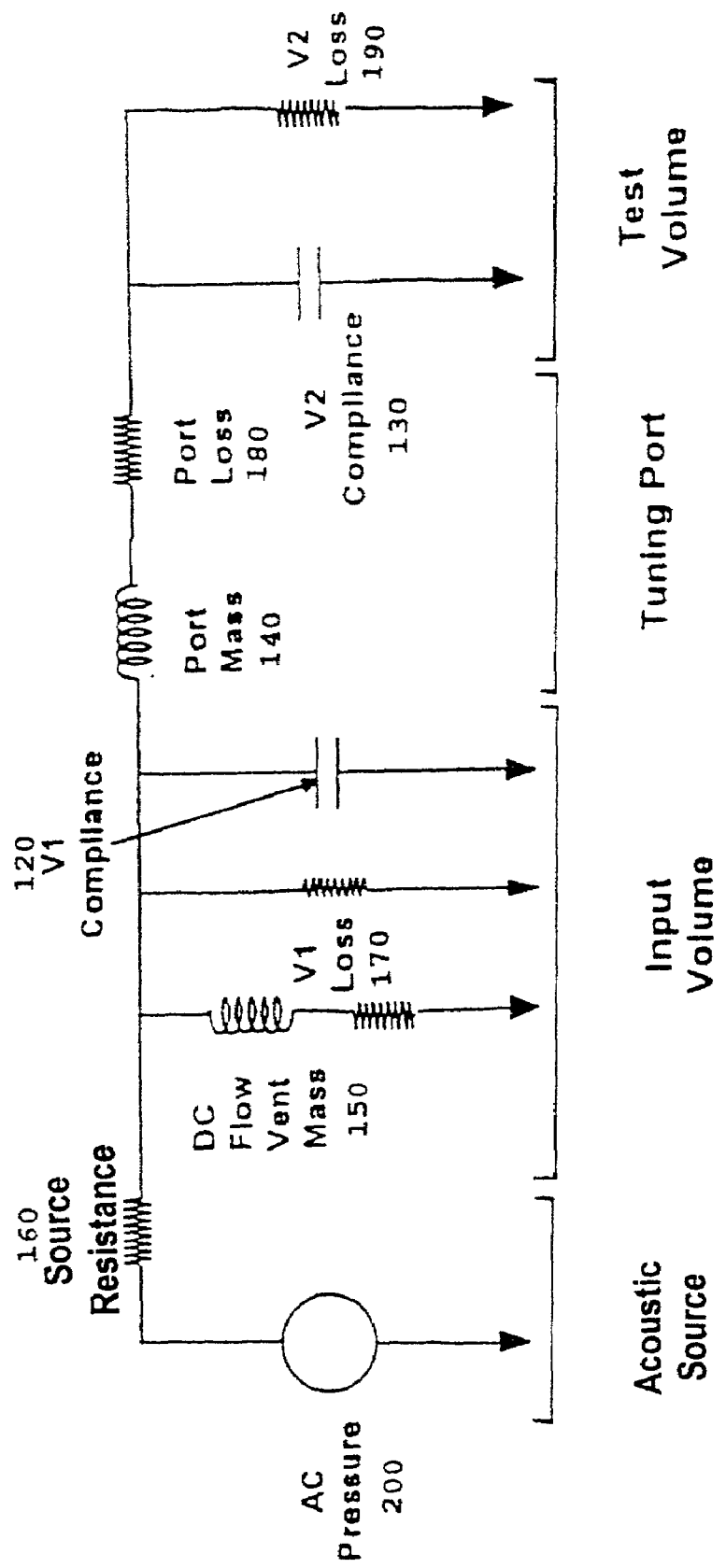
FIG. 3 illustrates another embodiment of the present invention employing an electrical analog equivalent circuit of the dual volume acoustic test cell illustrated in FIG. 2.

An electrical circuit analog that illustrates the principle of the two-volume device, and that may be used to calculate its operating characteristics, is illustrated in FIG. 3. The volumes constitute acoustic compliances that correspond to electrical capacitances 120 and 130. The acoustic masses of the duct/tuning port and DC exhaust vent correspond to electrical inductances 140 and 150, respectively. Acoustic losses correspond to the resistances 160–190, with the flow modulator or other acoustic source being represented by a periodically varying pressure in series with an acoustic loss corresponding to resistance 160. The operating frequency of the circuit is determined by the series combination of the volume compliances 120 and 130 with the duct/tuning port mass 140.

It is to be understood that an electrical circuit analog of the first embodiment, as illustrated in FIG. 1, is a simplification of FIG. 3 in which elements 130, 140, 180 and 190 are eliminated, the compliance 120 becomes that of the single test cell or chamber, and the flow vent mass 150 and vent acoustic loss 170 become the tuning port mass and loss, respectively. In this case, the operating frequency of the circuit is determined by the parallel combination of the chamber compliance 120 and the vent/port mass 150.

From the foregoing it will be obvious to one skilled in the art that numerous modifications and variations can be made without departing from the spirit and scope of the novel aspects of the current invention. For example, the same arrangements of components, appropriately sized, may be applied at frequencies outside the 1 Hz to 30 Hz infrasonic to low-sonic frequency range and there may be more than one external source for acoustic fields coupled to a multi-cell acoustic test apparatus. It is to be understood that no limitation of the scope of the present invention with respect to the specific embodiments illustrated is intended or should be inferred, but the scope of the present invention is to be defined solely by the attached claims.

What is claimed is:

1. A method for subjecting a test subject to an acoustical field comprising:
   supplying a chamber encompassing an input volume and having an inlet; supplying another chamber encompassing a test volume:
   interconnecting said chamber to said another chamber with a tuning port which forms a Helmholtz resonator interconnecting said input volume to said test volume;
   positioning the test subject within said test volume; and
   applying a periodic acoustic signal having a predetermined driving frequency from an acoustic energy source into said input volume through said inlet to establish an acoustic field in said input volume;
   coupling the acoustic field in said input volume to the test volume of said another chamber through said tuning port which forms a Helmholtz resonator tuned to said predetermined driving frequency whereby a test subject in said test volume is subjected to a resonance amplified periodic acoustic field at said predetermined driving frequency while the test volume is isolated from the acoustic energy sources;
   applying a sequence of periodic acoustic signals at different driving frequencies into said input volume: and
   physically adjusting said tuning port to tune the Helmholtz resonator to each of said different driving frequencies to thereby subject the test subject to a resonance amplified periodic acoustic field in said test volume at each of said different driving frequencies.

2. A method according to claim 1 further including the step of:
   exhausting air from said input volume to the exterior of said chamber through a high acoustic mass unit.

3. A method according to claim 1 wherein
   said acoustic energy source provides a source flow of one of air and gas; and further including the step of:
   modulating the source flow.

4. An acoustical test cell apparatus for subjecting a test subject to an acoustic field comprising:
   a chamber encompassing an input volume and having an inlet;
   another chamber encompassing a test volume;
   a tuning port interconnecting said chamber to said another chamber to form a Helmholtz resonator interconnecting said input volume to said test volume and being tuned to resonate at a particular frequency;
   an acoustic energy source for providing a periodic acoustic signal at said particular frequency into said input volume through said inlet whereby a test subject in said test volume is subjected to a resonance amplified periodic acoustic field at said particular frequency while the test volume is isolated from the acoustic energy source;
   said acoustic energy source being capable of providing a periodic acoustic signal at each of different particular frequencies; and
   the Helmholtz resonator being physically tuned to each of said different particular frequencies to amplify the intensity of the acoustic field in said test volume to thereby subject the test subject to a high intensity acoustic field at each of said different particular frequencies.

5. The acoustical test cell apparatus of claim 4 wherein:
   said tuning port has a variable geometry for setting the tuning of the Helmholtz resonator.

6. The acoustical test cell apparatus of claim 4 wherein:
   said chamber has an outlet; and further including an exhaust means having a high acoustic mass at said outlet for exhausting air from said input volume to the chamber exterior.

7. The acoustical test cell apparatus of claim 6 wherein:
   said exhaust means is an elongated, small-aperture duct proportioned to only pass acoustic energy at frequencies below the frequency of said acoustic energy source.

8. The acoustical test cell apparatus of claim 7 wherein:
   said acoustic energy source provides a compressed air flow; and further including a flow modulator for regulating the flow into the input volume of said chamber.

9. The acoustical test cell apparatus of claim 8 wherein:
   said another chamber further includes a low-volume positive-pressure ventilating air input having a high acoustic mass.

10. An electrical circuit which constitutes an analog of an acoustic test cell apparatus employing a periodic high intensity acoustic field, said apparatus comprising;

a chamber encompassing a volume;

means for generating a sequence of periodic high-intensity acoustic fields within said volume having different predetermined frequencies and intensities;

an external source directly coupled to said volume for providing said periodic high intensity acoustic fields; and a tuning port connected to said volume for tuning said frequency of said high intensity acoustic field within said volume to a predetermined frequency and intensity, said tuning port being not directly connected with said external source;

and wherein:

said chamber is rigid and airtight, said acoustic field is continuous; and said tuner and said volume form a Helmholtz resonator being physically tuned to each of said different predetermined frequencies to amplify the intensity of the acoustic field in said test volume to thereby subject the test subject to a high intensity acoustic field at each of said different predetermined frequencies;

and wherein said volume further comprises:

an input volume and a test volume, said test volume being acoustically isolated from both said source flow and said input volume and connected to said input volume by said associate tuning port; and a high acoustic mass means for exhausting air from said input volume to the exterior comprising:

an air flow modulator circuit providing a continuous field, comprising;

an AC power source providing a voltage source representing a periodically varying gas pressure source, and a resistance element representing the flow resistance of a gas flow modulator having said resistance element connected in series with said AC power source;

an input volume circuit in series with said field source comprising:

an inductance element representing a high acoustic mass in series with a resistance element that represents acoustic losses associated with said acoustic mass, a capacitance element representing an input volume in parallel with said high acoustic mass , and a resistance element representing acoustic loss in an input volume in parallel with said input volume;

a tuning port circuit in series with said input volume circuit and comprising:

an inductance element providing a tuning port mass, and a resistance element representing acoustic loss in a tuning port in series with said inductance element;

a test volume circuit in series with said tuning port circuit and comprising a capacitance element representing a test volume, and a resistance element representing acoustic loss in a test volume in parallel with said capacitance element;

wherein continuous DC current flow is varied periodically by said flow modulator circuit and is directly coupled with said input volume said input volume is vented by said high acoustic mass and is tuned by said tuning port to produce a predetermined AC voltage representing an acoustic signal in said test volume.

* * * * *